(12) United States Patent
Porter et al.

(10) Patent No.: US 8,852,933 B2
(45) Date of Patent: Oct. 7, 2014

(54) DEFORMABLE TRANSPORTABLE BIOREACTOR CHAMBER

(71) Applicant: Illinois Tool Works Inc., Glenview, IL (US)

(72) Inventors: Blaise Damian Porter, Minneapolis, MN (US); Kent Vilendrer, Eden Prairie, MN (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 13/945,518

(22) Filed: Jul. 18, 2013

(65) Prior Publication Data

US 2013/0302897 A1 Nov. 14, 2013

Related U.S. Application Data

(62) Division of application No. 12/418,371, filed on Apr. 3, 2009, now Pat. No. 8,492,135.

(51) Int. Cl.
| | |
|---|---|
| *C12N 5/00* | (2006.01) |
| *C12N 5/02* | (2006.01) |
| *C12M 1/00* | (2006.01) |
| *C12M 1/12* | (2006.01) |
| *C12M 3/00* | (2006.01) |
| *C12M 1/34* | (2006.01) |

(52) U.S. Cl.
CPC .............. *C12N 5/0068* (2013.01); *C12M 23/46* (2013.01); *C12M 41/40* (2013.01); *C12M 23/26* (2013.01); *C12M 41/44* (2013.01)
USPC ........ 435/325; 435/395; 435/401; 435/283.1; 435/297.1

(58) Field of Classification Search
CPC combination set(s) only.
See application file for complete search history.

(56) References Cited

U.S. PATENT DOCUMENTS

| | | |
|---|---|---|
| 3,651,607 A | 3/1972 | Lee, II |
| 4,130,120 A | 12/1978 | Kohler, Jr. |
| 5,460,968 A | 10/1995 | Yoshida et al. |
| 5,670,708 A | 9/1997 | Vilendrer |
| 6,060,306 A | 5/2000 | Flatt et al. |
| 6,121,042 A | 9/2000 | Peterson et al. |
| 6,218,187 B1 | 4/2001 | Finer et al. |
| 6,432,698 B1 | 8/2002 | Gaugler et al. |
| 6,544,788 B2 | 4/2003 | Singh |
| 6,547,783 B1 | 4/2003 | Vilendrer et al. |
| 6,673,598 B1 | 1/2004 | Akers et al. |
| 6,794,184 B1 | 9/2004 | Mohr et al. |
| 6,855,542 B2 | 2/2005 | Demilla et al. |
| 6,979,308 B1 | 12/2005 | MacDonald et al. |
| 7,033,823 B2 | 4/2006 | Chang |
| 7,122,371 B1 | 10/2006 | Ma |
| 7,179,287 B2 | 2/2007 | Wolfinbarger, Jr. |

(Continued)

OTHER PUBLICATIONS

Raif et al. (2007) Tissue Engineering vol. 13, No. 3, pp. 629-640.*

(Continued)

*Primary Examiner* — Chris R Tate
*Assistant Examiner* — Douglas F White
(74) *Attorney, Agent, or Firm* — McCarter & English, LLP

(57) ABSTRACT

An apparatus and method is described for seeding and culturing cells on a sample. The apparatus includes a chamber in which the volume of the chamber may be adjusted without compromising the seal or sterility of the chamber. The apparatus enables the seeding of cells in a reduced volume and culturing of cells in an increased volume. Further, the apparatus enables application of forces, strains and torques to a sample during seeding, culturing or transportation of the sample.

19 Claims, 12 Drawing Sheets

(56) References Cited

U.S. PATENT DOCUMENTS

| | | | |
|---|---|---|---|
| 7,198,940 | B2 | 4/2007 | Vellinger et al. |
| 7,229,820 | B2 | 6/2007 | Wilson |
| 7,270,472 | B2 | 9/2007 | Carreras |
| 7,348,175 | B2 | 3/2008 | Vilendrer et al. |
| 7,348,176 | B2 | 3/2008 | Demilla et al. |
| 7,371,567 | B2 | 5/2008 | Galavotti |
| 7,410,792 | B2 | 8/2008 | Vilendrer |
| 7,472,604 | B2 | 1/2009 | Moore, Jr. et al. |
| 7,587,949 | B2 | 9/2009 | Dingmann et al. |
| 7,624,648 | B2 | 12/2009 | Nickel et al. |
| 7,694,593 | B2 | 4/2010 | Owens et al. |
| 2006/0141607 | A1* | 6/2006 | Wikswo et al. ............ 435/287.1 |
| 2008/0068920 | A1 | 3/2008 | Galliher et al. |
| 2008/0274545 | A1 | 11/2008 | Kuo et al. |

OTHER PUBLICATIONS

Lyons et al. Annals of Biomedical Engineering, vol. 31, pp. 1017-1030, 2003.*

Christopher M. Voge, Mihalis Kariolis, Rebecca A. MacDonald, Jan P. Stegemann, "Directional Conductivity in Protein-Nanotube Biomaterials through Strain-Induced Matrix Alignment", presented at 8th World Biomaterials Congress. Amsterdam, Netherlands, Jun. 2008.

Patrick Whitlcok, James Knutson, Thomas L. Smith, Mark E. Van Dyke, Jeffrey S. Shilt, L. Andrew Koman, Gary G. Poehling, "Effects of Mechanical Stimulation on a Cell-Seeded Scaffold Developed for Tendon and Ligament Regeneration" presented at Transactions of the 6th Combined Meeting of the Orthopaedic Research Society, Honolulu, Hawaii, Oct. 2007 and at Transactions of the 54th Annual Orthopaedic Research Society Meeting, San Francisco, California, Mar. 2008.

Blaise D. Porter, Angela S Lin, Alexandra Peister, Dietmar Hutmacher, Robert Guldberg, "Noninvasive image analysis of 3D construct mineralization in a perfusion bioreactor", Biomaterials. May 28, 2007(15): p. 2525-33. Epub Jan. 26, 2007.

* cited by examiner

US 8,852,933 B2

DEFORMABLE TRANSPORTABLE BIOREACTOR CHAMBER

CROSS-REFERENCE TO RELATED APPLICATIONS

This application claims the filing benefit and priority of U.S. Non-Provisional Application Serial No. 12/418,371 filed Apr. 3, 2009, the contents of which are incorporated herein by reference in its entirety.

FEDERAL SPONSORSHIP

Not Applicable

JOINT RESEARCH AGREEMENT

Not Applicable

TECHNICAL FIELD

This invention pertains generally to cell seeding and cell tissue growth. This invention also pertains to flexible, deformable, chambers suitable for seeding and growing cells on a sample within a sterile interior of the chamber.

BACKGROUND

Generally, the seeding or depositing of cells and subsequent growth or culture of cells has previously been described. In the past, cells have been seeded and cultured on a matrix, specimen, tissue, vascular graft, biomedical prosthesis, substrate, and other medical devices (hereinafter referred to simply as a sample or specimen). Some prior systems seed cells on a sample in a seeding chamber and then transfer the sample to a growth chamber, where nutrients are supplied to the cells for growth. Other systems have used pressure or other fluid forces to influence adhesion of the cells on the sample. It has been recognized that cells seeded or cultured in a dynamic fluidic environment are more likely to tolerate physiological conditions of the human body.

Other prior devices have cultured a sample within a disposable bag. It has been recognized that lack of a framework for the bag during transport is not preferred. Other user criteria may further influence the acceptance and use of a particular chamber including the ease of transport, scalability of the chamber to accommodate varying length and widths of a sample, and versatility of chamber for use while seeding, culturing or testing a sample in a sterile environment. Further, it is now recognized that it is advantageous to provide a dynamic environment that allows a constant or varying strain or other forces applied to the sample during seeding, culture, testing and transport.

SUMMARY

Embodiments of the invention include an apparatus and method for seeding, culturing, testing, and transporting a sample without removing the sample from a sterile chamber of the apparatus. The chamber has a volume that is adjustable such that cells may be seeded on the sample in a reduced volume and cells may be cultured on the sample in an expanded volume. Further, in an embodiment of the invention, the chamber includes a first deformable outer sheath and second deformable inner enclosure. Also, a dual membrane chamber of the invention may be transported while maintaining the sterility of the interior membrane of the chamber.

During seeding and culturing cells on the sample, linear forces, strains, and torques may be applied to the sample within the chamber. Further, the chamber may be transported while maintaining a linear force, strain or torque applied to the sample. Alternatively, in an embodiment of the invention, the volume of the chamber may be varied while applying varied linear forces, strains and torques on the sample. Also, in an embodiment of the invention the volume is varied with the aid of a mold that constricts a portion of the chamber, thereby reducing the volume. Additionally, fluids may be delivered into the chamber causing the chamber to expand to an increased volume.

Also described herein are grips contained within the chamber. The grips have an adjustable separation distance between the grips. Further, an installation and indexing frame is coupled to the chamber to facilitate a repeatable gauge length of multiple samples and to provide support to the chamber during transport. To facilitate loading of a sample in the grips a first end of the chamber may be drawn towards the second end to expose a space between the grips. In this manner the space between the grips is accessible from multiple angles.

The accompanying drawings, which are incorporated in and constitute a portion of this specification, illustrate embodiments of the invention and, together with the detailed description, serve to further explain the invention. The embodiments illustrated herein are presently preferred; however, it should be understood, that the invention is not limited to the precise arrangements and instrumentalities shown. For a fuller understanding of the nature and advantages of the invention, reference should be made to the detailed description in conjunction with the accompanying drawings.

DESCRIPTION OF THE DRAWINGS

In the various figures, which are not necessarily drawn to scale, like numerals throughout the figures identify substantially similar components.

DETAILED DESCRIPTION

Figure 1:
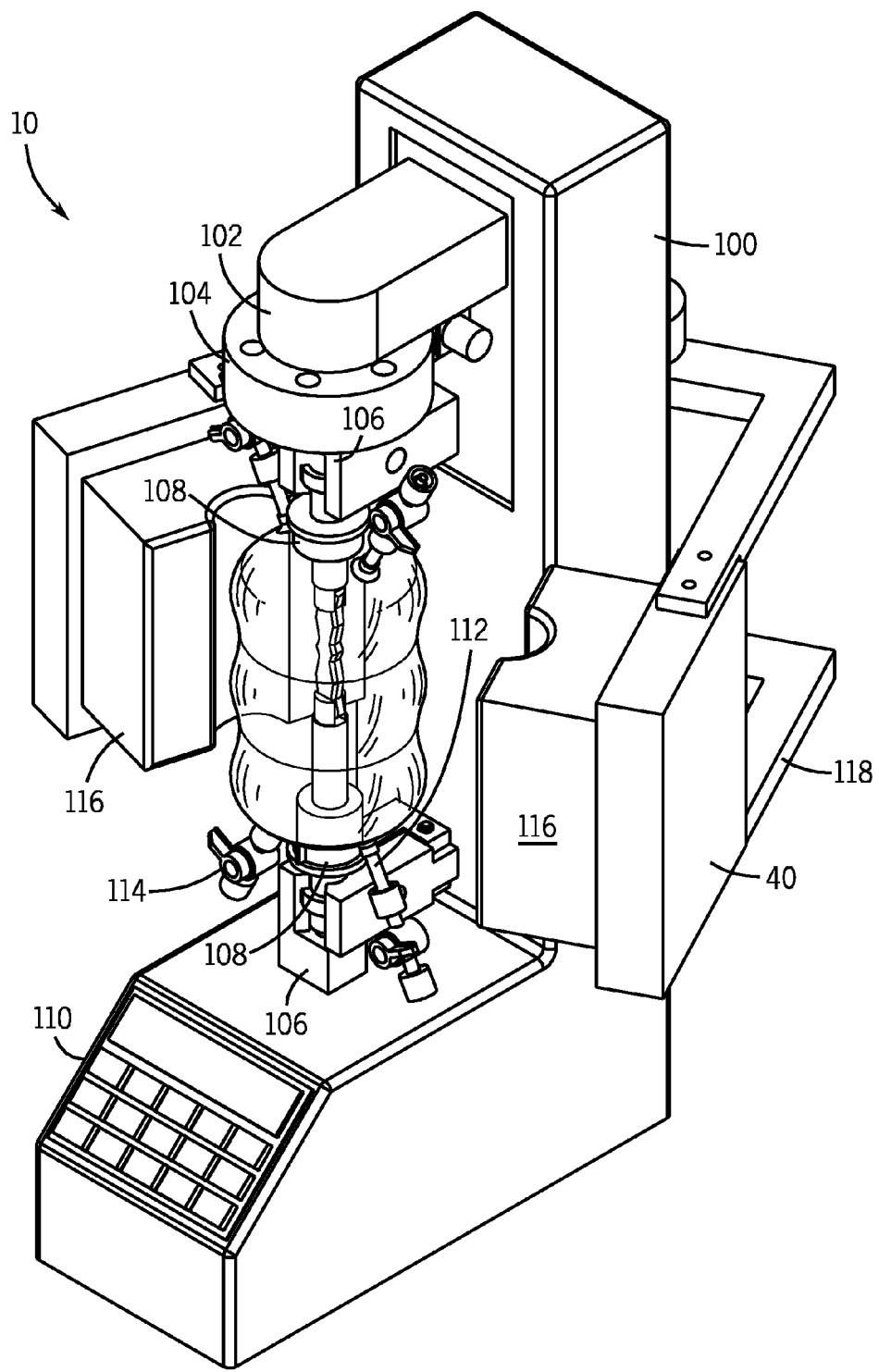
FIG. 1 is a perspective view of a bioreactor and chamber in accordance with an embodiment of the invention.

The following description provides detail of various embodiments of the invention, one or more examples of which are set forth below. Each of these embodiments are provided by way of explanation of the invention, and not intended to be a limitation of the invention. Further, those skilled in the art will appreciate that various modifications and variations may be made in the present invention without departing from the scope or spirit of the invention. By way of example, those skilled in the art will recognize that features illustrated or described as part of one embodiment, may be used in another embodiment to yield a still further embodiment. Thus, it is intended that the present invention also cover such modifications and variations that come within the scope of the appended claims and their equivalents.

The bioreactor of the present invention includes a chamber capable of retaining fluids within the chamber and has a first expanded volume and second constricted volume. The volume of the chamber increases and decreases without adding or eliminating wall segments to the chamber. Alternatively, the chamber may include a first deformable outer sheath and second deformable inner enclosure. Ports may be coupled to the chamber and, in particular, may be coupled in fluid communication to the outer sheath and inner enclosure. Further, valves may be coupled to the ports to control the flow of fluids through the ports and may be utilized to assist hydrostatic pressure within the chamber.

The bioreactor includes grips containable within the chamber. A first end of each grip contained within the chamber is suitable for gripping a portion of a sample. A second end of each grip is suitable for coupling to a connector of the bioreactor. When coupled to the bioreactor, stepper motors or drivers of known suitable construction selectively deliver axial, linear and torsion loads on the grips while contained in the chamber. A controller may be utilized to control the motors and drivers and selectively apply forces, strains and torques to one or both grips. The chamber has first and second ends, wherein the first end may be drawn towards the second end to expose a space between the grips. With the space exposed, a sample is easily loaded and unloaded to and from the grips.

A user may use the apparatus to seed and culture cells on a sample within the chamber. The user positions a sample within the chamber. The sample may be held in place within the chamber by grips that are also contained within the chamber. A distance between the grips is controllable such that the gauge length of the sample held between the grips may be approximately equivalent among several samples. The chamber is capable of retaining fluids therein.

Further, the user may selectively constrict the chamber so that it has a reduced volume during seeding and the chamber may be selectively expanded to have an increased volume during culturing and testing the sample. Those skilled in the art will appreciate that it may be desired to vary the volume of the chamber during the culturing and testing of the sample.

Once the sample is grasped between the grips, the user may selectively control the bioreactor such that linear forces, strains and torques are applied to the sample. This stimulus to the sample may be applied while the sample is contained within the chamber under a seal and may be applied before, during or after seeding and/or culturing the sample. The user may couple an installation and indexing frame to ends of the grip extending from the chamber. Once coupled to the grips, the chamber may be removed from the bioreactor. The indexing frame couples to the grips and retains the separation distance between the grips. Any torque, and axial or linear forces applied to the grips will also be retained in the indexing frame. In this manner, the user may transport the sample within the sterile chamber interior with a continuous force, strain or torque applied to the sample.

Figure 2:
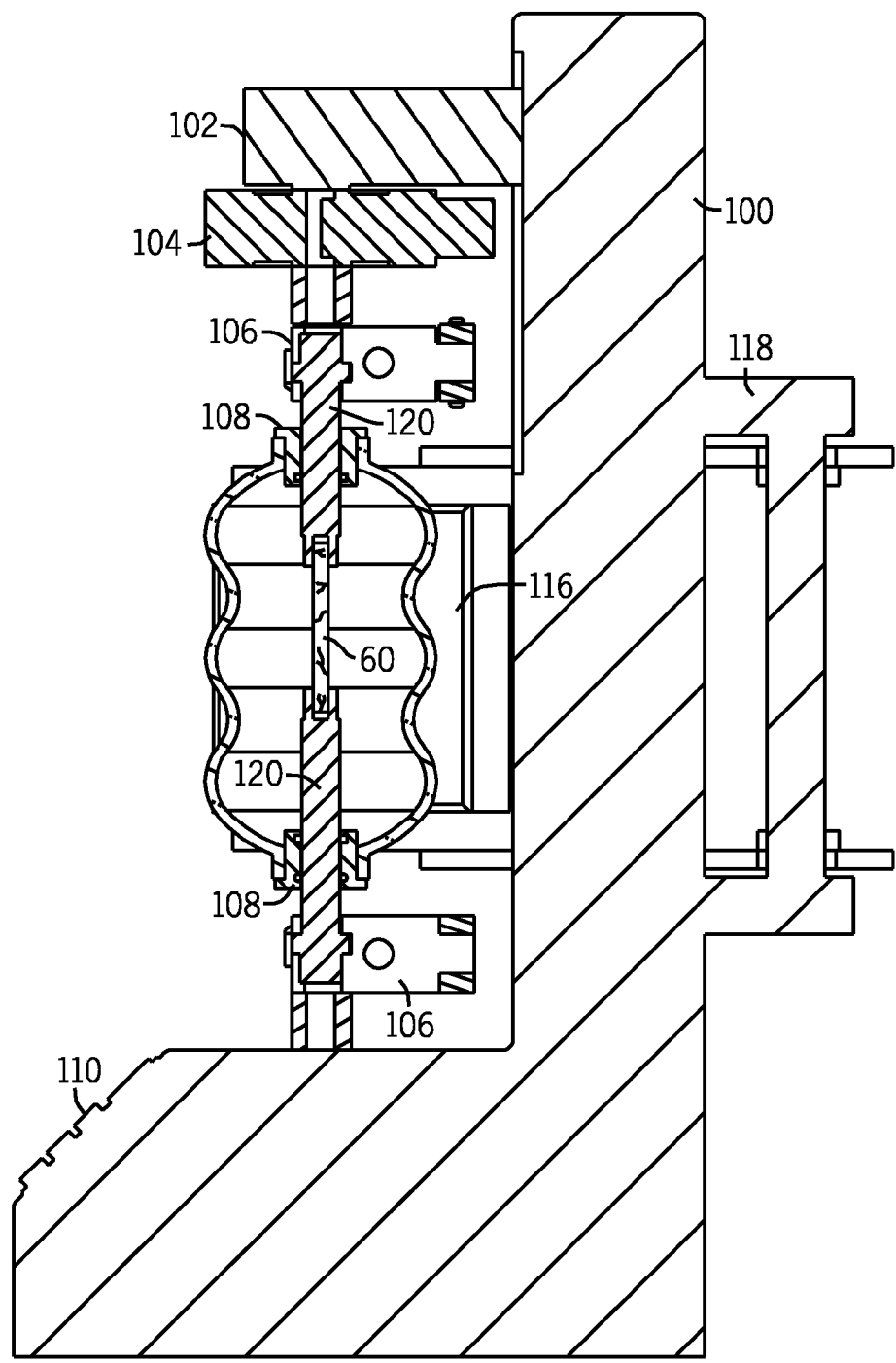
FIG. 2 is a partial sectional view of the bioreactor and chamber of the type shown in FIG. 1.

Turning attention now to the Figures, embodiments of the bioreactor or system 10 of the present invention will now be described in more detail. Referring first to FIGS. 1-2, the bioreactor 10 includes a frame 100, drive assembly 102, load cell 104, quick disconnect coupling 106, controller 110, and mold cavity 116 supported by mold arms 118. Although the chamber is shown in FIG. 2 as opaque, those skilled in the art will appreciate that at least a portion of the chamber may be constructed from a translucent material. Drive assembly 102 may be coupled to a linear or axial actuator (not shown) contained with frame 100. The drive assembly 102 and linear actuator may be of a servo pneumatic, electromechanical flexure bearing or electromechanical linear screw motors of known suitable construction. The drive assembly 102 and linear actuator are coupled to the load cell 104, couplings 106 and frame 100 so that the couplings 106 may be rotated and the space between the couplings 106 may be increased or decreased in a controlled finite manner.

The controller 110 is electrically coupled to the drive assembly 102, load cell 104, linear actuator and sensors (not shown) so that feedback and analysis loops may be incorporated into the controller 110 to selectively provide repetitive, continuous, and intermittent stimulus to a sample 60 held in place between couplings 106. As the connector 106 is rotated, a resulting torque is applied to the sample 60. Further, the controller 110 may be utilized to alter a separation distance between the connectors 106, thereby applying strains or axial and linear forces on the sample 60. The controller 110 further allows the user to maintain the position of the connectors 106 in a fixed position to thereby translate a fixed strain, force or torque on the sample 60. In this manner a variety of stimulus sequences may be applied to a selected sample 60.

It will be appreciated by those skilled in the art that setting, monitoring and controlling the separation distance between the connectors enables finite control of the stimulus applied to the sample. Further, sensors may be electrically coupled to the controller 110 to detect the position of the top and bottom grips 120. This displacement may be measured with, by way of illustration and without limitation, an LVDT, laser PSD, incremental encoder, or other measurement feedback device of known suitable construction. Under load control, the controller 110 adjusts the separation distance and positions of the couplings 106 and grips 120 so that a known force (common preload) may be applied to all samples 60. The load cell 104 may also be utilized to control the force applied to the sample. Also, controlling the resulting distance between the grips 120 with a preload applied to the sample 60 allows the user to set a consistent gauge length to multiple samples.

Figure 3:
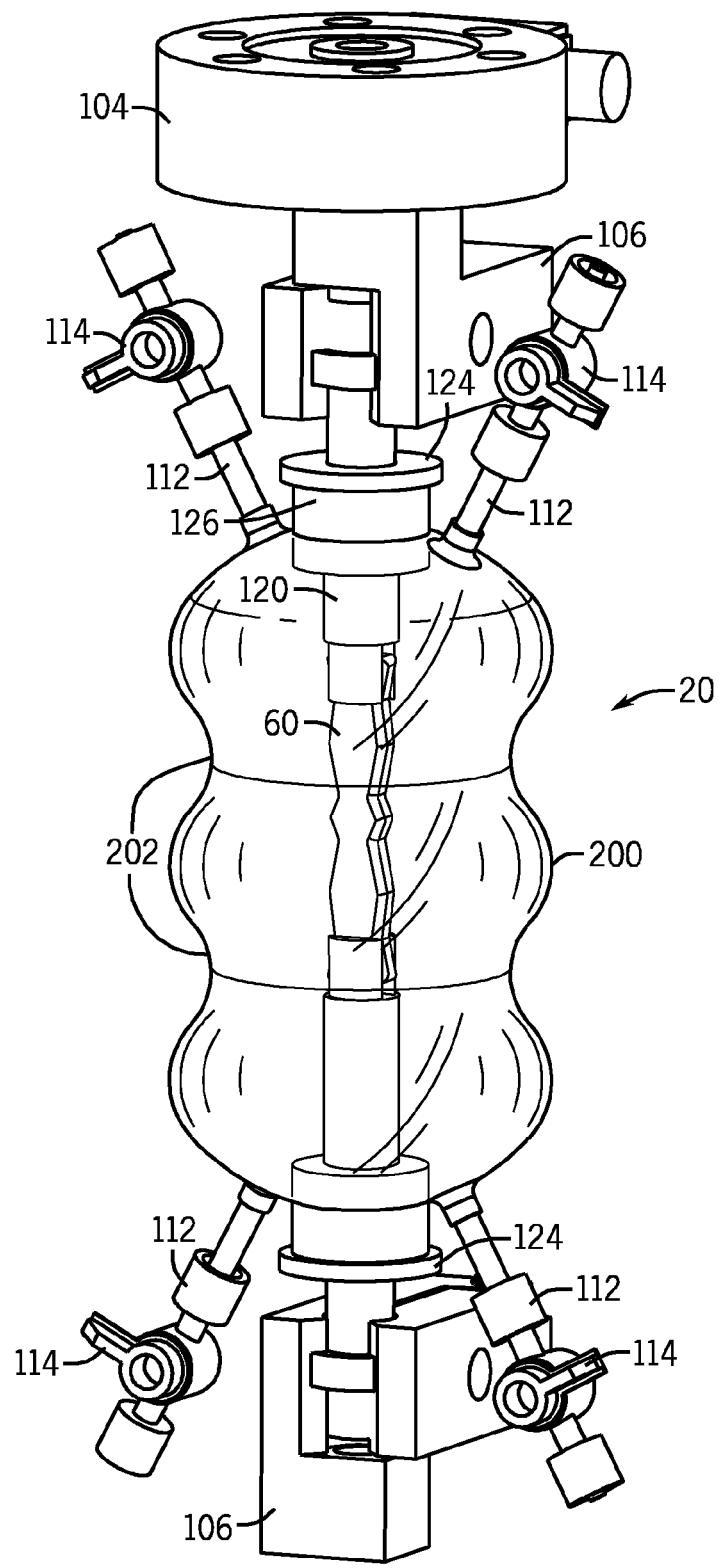
FIG. 3 is a perspective view of a bioreactor chamber in accordance with an embodiment of the invention, shown coupled to a portion of a bioreactor.

FIG. 3 shows a single chamber 20 of the present invention including a sheath or bag 200 having opposite ends affixed to feed through connectors 108. Grips 120 engage and slide within the feed through connectors 108 and an o-ring or seal (refer to FIG. 11) restricts fluids from passing between the grip 120 and connector 108. Alternatively, the seal may act as a deformable feed through that facilitates axial and/or rotational motion with respect to the connector 108. For example, without limitation, the seal could include a mini bellow of known suitable construction. An end of each grip 120 is thereby sealed and contained within the sheath 200. The other end of the grip 120 is coupled within a quick disconnect coupling 106. The sample may be secured to the grips in a manner suitable to keep the ends of the sample from slipping in the grips. By way of example, grips 120 may be a suitable construction adapted for holding a tissue, vascular grafts, biomedical prosthesis, medical devices or other desired specimen or sample. Further, by way of example and without limitation intended, a tubular sample may slip over and be secured to an end of grips 120 and a relatively planar sample may be clamped or sutured to an end of the grips 120.

Connectors 108 include a flange 124 formed on the end thereof and an end of the bag 200 is affixed to a shoulder 126 of the connector 108. The flange 124 may serve as a stop for the end of bag 200. Ports 112, of suitable known construction, may be coupled to an exterior of the sheath 200 in a known manner to provide a seal between the port 112 and the sheath 200. Further valves 114 may be coupled to the ports to control the ingress and egress of fluids through port 112 and to control hydrostatic pressure within the chamber. Further, ports 112 may be located at the top of the sheath 200 to facilitate delivery of cells and media into the interior of the chamber 20 and ports 112 may be located at the bottom of the sheath 200 to act as a drain and facilitate media exchange as well as acquiring media samples.

The exterior of each bag may include indicia, tags, chips or other device to identify the chamber 20 for tracking and monitoring the particular sample 60 contained within the chamber 20. The sheath 200 is flexible and may include horizontal folds 202 and vertical folds (not shown). In an embodiment of the invention the various components of the chamber are manufactured from materials suitable for sterilization and preferably suitable for autoclave. The walls of sheath 200, 300 and enclosure 302 may be constructed from a gas permeable, flexible, stable, durable, low durometer material capable to withstand autoclave, exposure to ethylene oxide, or gamma sterilization. Further, the preferably selected material is a translucent material that aids in the monitoring of the sample within the chamber. One such suitable material is a platinum cured silicone.

The sheath 200, 300 and enclosure 302 may, for example, be constructed from two sheets of material welded together at seems, in accordance with techniques known in the art (for example, IV fluid bags). Alternatively, the sheath 200, 300 and enclosure 302 may be molded, or extruded. Further, the ends of the sheath 200, 300 and enclosure 302 may be sealed to the connector by heat, ultrasound or radiowave welding, or by other known suitable means of sealing them together. Alternatively, one end may be molded into the connector 108.

Figure 4:
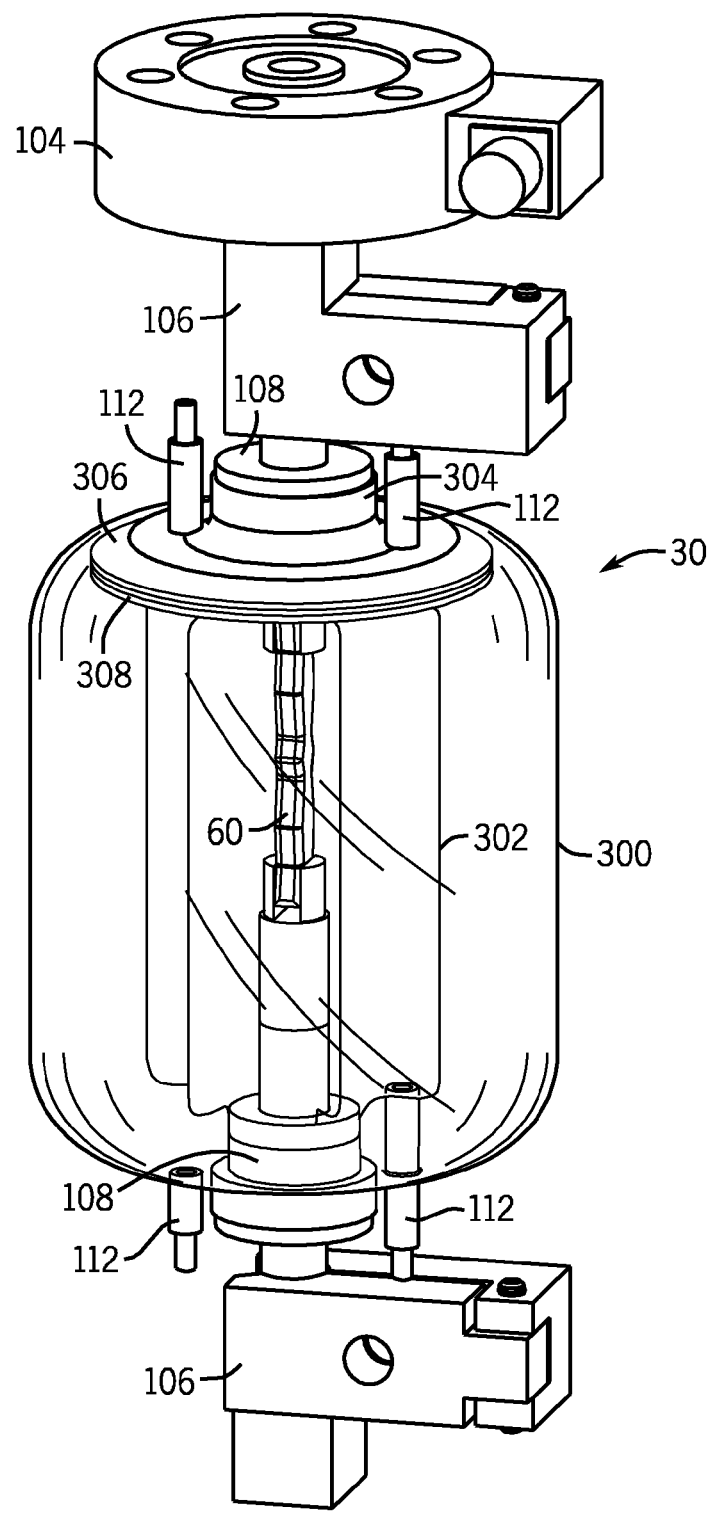
FIG. 4 is a perspective view of a chamber in accordance with an embodiment of the invention, shown coupled to a portion of a bioreactor.
Figure 5:
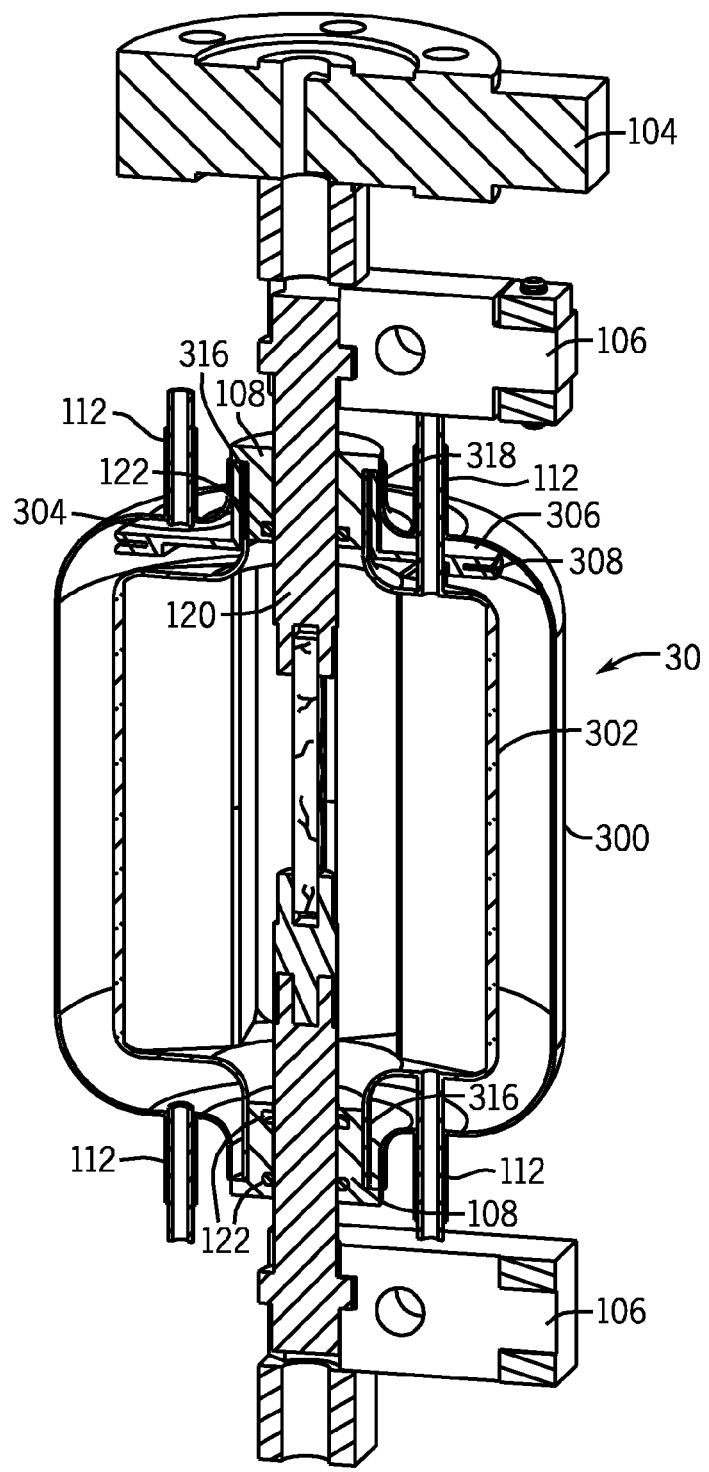
FIG. 5 is a partial sectional perspective view of the chamber of the type shown in FIG. 4 and shown coupled to a portion of a bioreactor.
Figure 12:
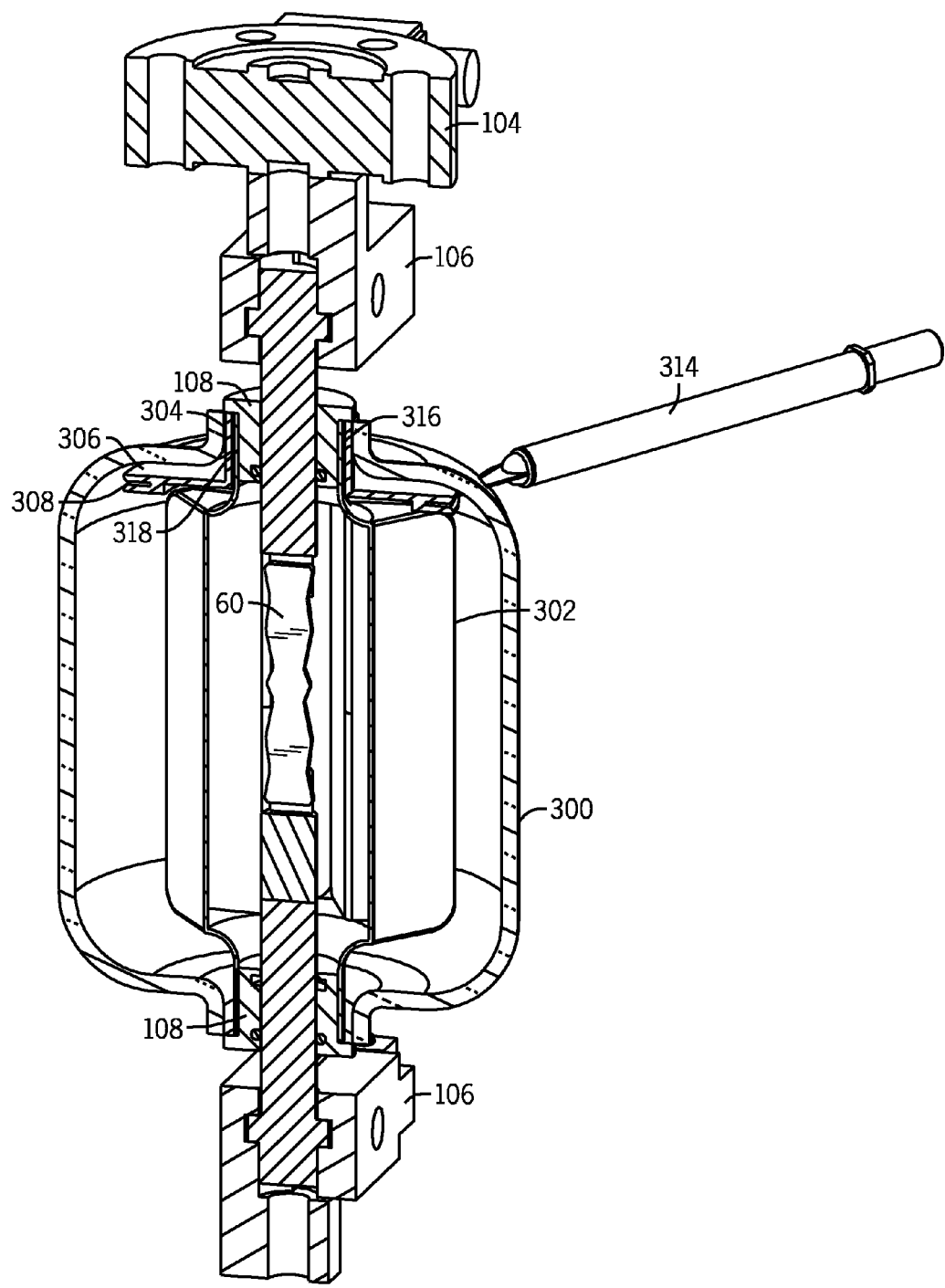
FIG. 12 is a partial sectional perspective view of a bioreactor chamber in accordance with an embodiment of the invention, shown coupled to a portion of a bioreactor and with ports and valves removed.

FIGS. 4 and 5 show generally a chamber 30 having a dual membrane. The chamber 30 includes an outer sheath 300 and inner enclosure 302. Disc 306 is positioned between sheath 300 and enclosure 302, separating an upper portion of the sheath 300 and enclosure 302. A shoulder 304 of the disc 306 is sized to slip over the outside of connector 108 with an end of the inner enclosure 302 sandwiched and creating a seal between the disc 306 and connector 108. An end of the sheath 300 is affixed to an outer surface of the shoulder 304 of disc 306 creating a seal between the sheath 300 and disc 306. A groove 308 is formed on an outer edge of the disc 306. A knife 314 blade follows the groove 308 to open the outer sheath 300 without compromising the sterile environment of the enclosure 302 (see FIG. 12). Folds in the enclosure 302 and folds in the outer sheath 300 (not shown) may expand and open to increase a volume within the sheath 300 and enclosure 302.

Figure 6:
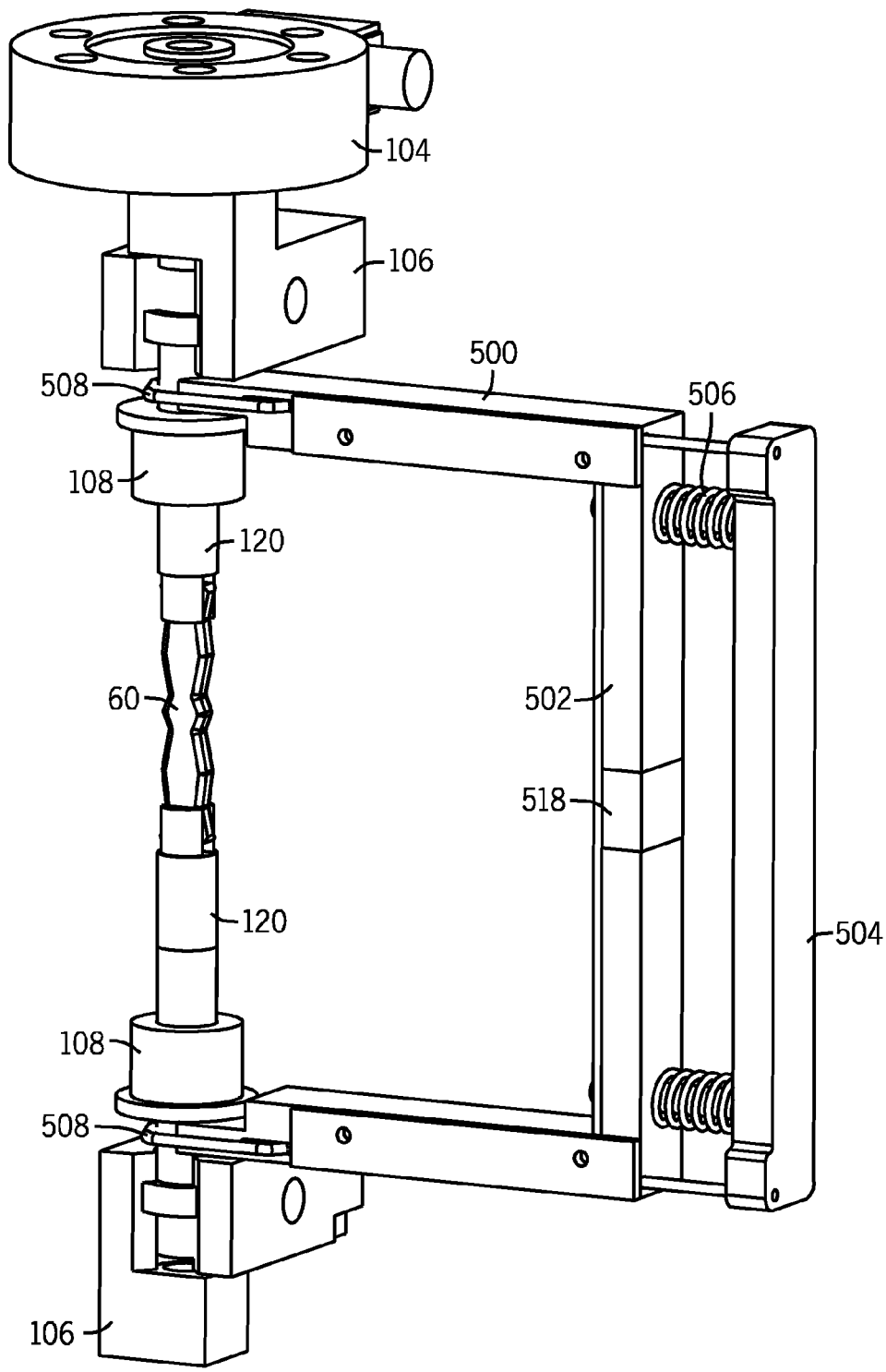
FIG. 6 is a perspective view of a bioreactor chamber installation aid in accordance with an embodiment of the invention, and shown couple to a portion of the bioreactor and a portion of a bioreactor chamber.
Figure 7:
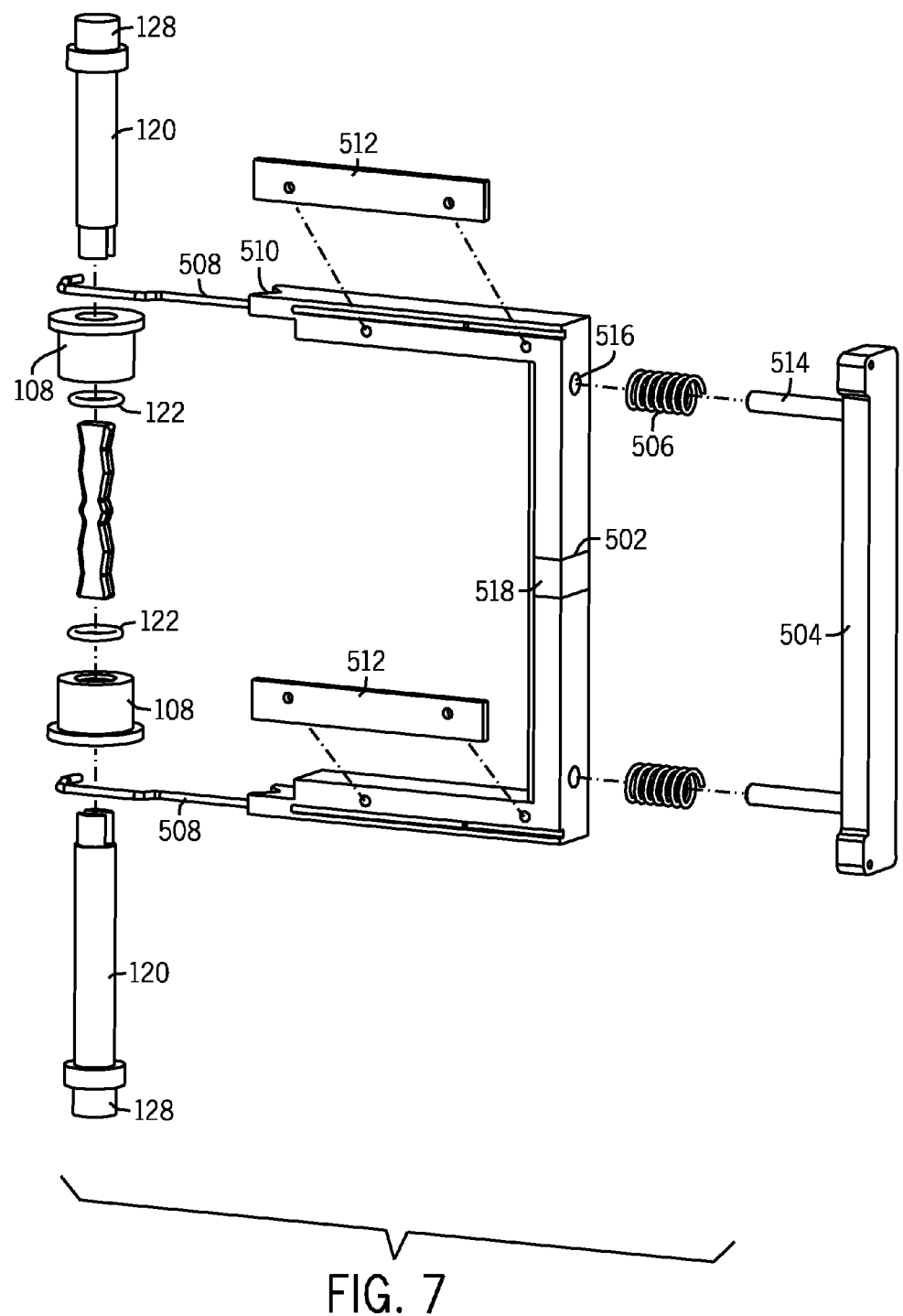
FIG. 7 is an exploded perspective view of the bioreactor chamber installation aid and exploded portion of the bioreactor chamber of the type shown in FIG. 6.

FIGS. 6 and 7 show an index frame 500 coupled to a portion of the chamber 20 and bioreactor 10. The frame 500 includes an expandable handle 502 having an expansion joint 518, a base 504, grabbers or fingers 508. A v-groove 510 is formed in the ends of frame 500 and positively engage with an ends of the grips 120. Finger 508 engages the grip on the opposite side and holds the grip 120 in the v-groove 510. The base 504 is actuated by a spring 506, and when squeezed towards the handle 502 an end of the finger 508 is pushed away from the v-groove 510. Finger plate 512 keeps the finger 508 in place along the frame 500. Pins 514 of the base 504 align with apertures 516 in the handle 502 and contain the springs 506 between the handle 502 and base 504. An end of the frame 500 may also engage with the flange 124 on the connector 108 to provide a controlled separation distance between the connectors 108. The expansion joint 518 may be adjusted to accommodate the length of the sample 60, independent of whether or not the sample 60 is under preload conditions. The mechanism to engage or fasten index frame 500 to connectors 108 is not limited to a spring loaded clamping mechanism. Without limitation, other suitable mechanisms may be incorporated, including a thumb screw, set screws, magnets, electro magnets, adhesives, Velcro™, suction, or other known fasteners.

Figure 8:
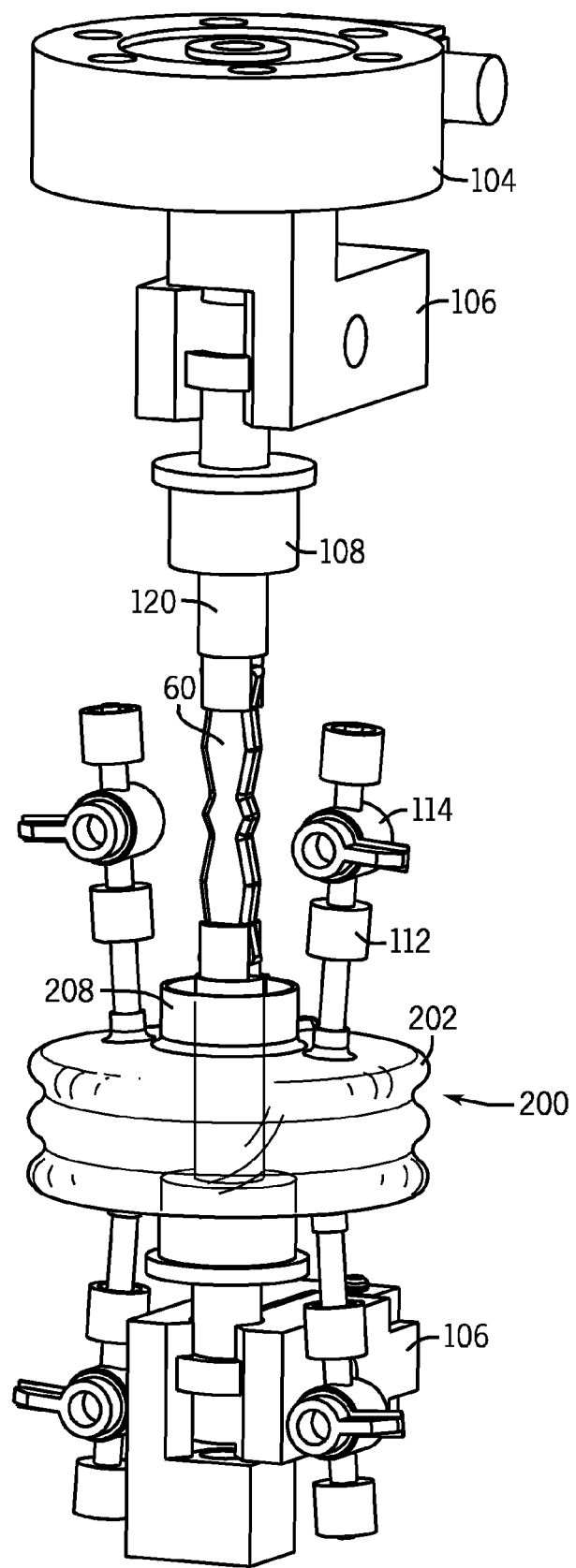
FIG. 8 is a perspective view of a bioreactor chamber in accordance with an embodiment of the invention, shown coupled to a portion of a bioreactor and showing one end of the chamber compressed towards the other end.

Having described the constructional features of embodiments of the invention, the mode of use will next be described. For discussion purposes, but without any limitation intended, use of the single chamber 20 will be described. With reference to FIG. 8, the user selects a chamber 20 and inserts each outer end of the grip 120 into the respective quick disconnect coupling 106 of bioreactor 10. The couplings 106 are locked and engaged to the grip 120 so that a rotation of the coupling 106 will simultaneously rotate the grip 120. The user then collapses the sheath 200 by drawing an upper end of the sheath 200 down towards a lower end of the sheath 200 exposing the interior ends of the grips 20. The user may then engage a sample 60 in the grip ends of the grip 120. The controller 110 is used to selectively determine the preload force and separation distance between the grips 120. The user then draws open end 208 of the sheath 200 over the connector 108 and affixes the sheath to the connector in a known manner to create a seal between the sheath 200 and connector 108.

Figure 9:
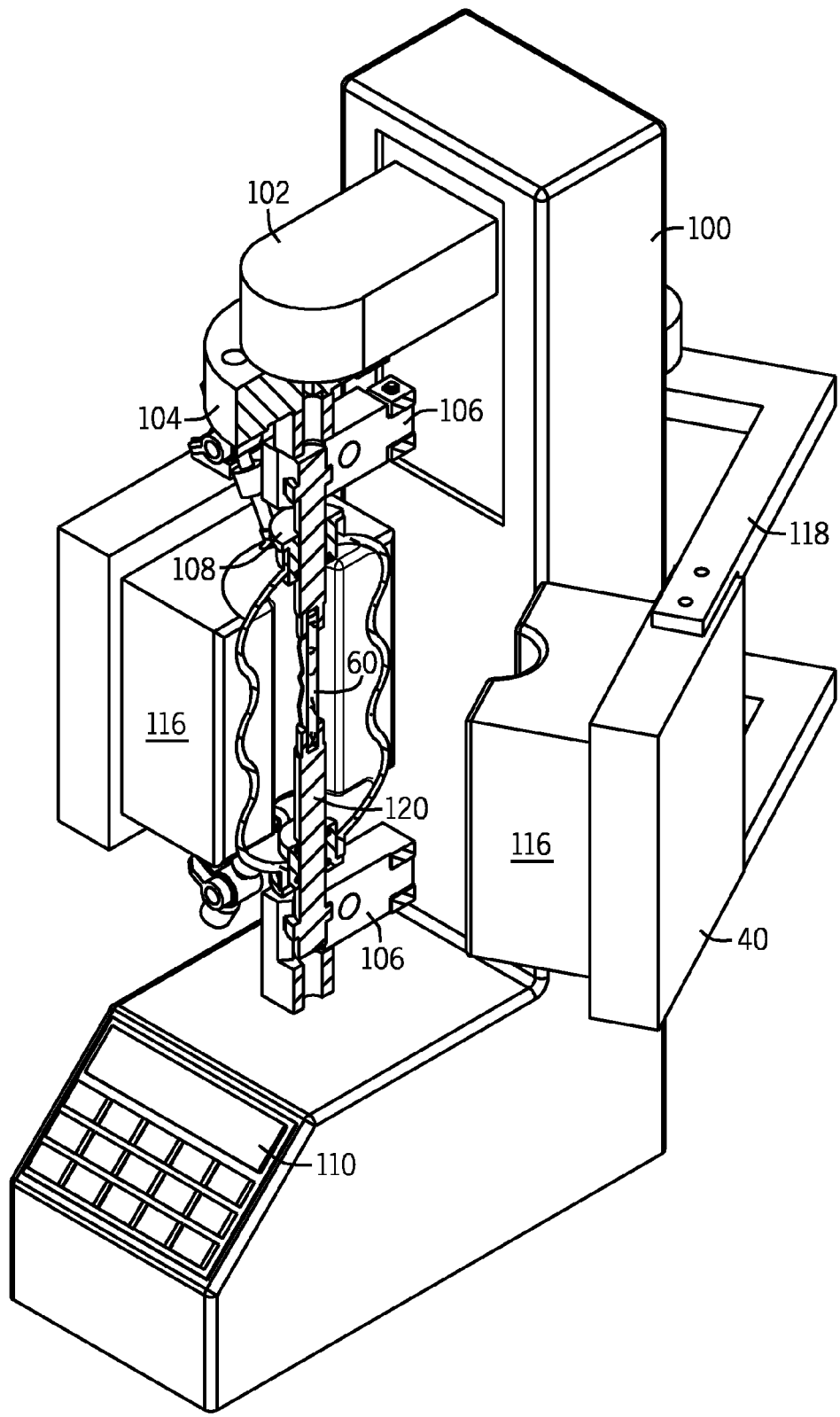
FIG. 9 is a partial section perspective view of a bioreactor and bioreactor chamber in accordance with an embodiment of the invention showing the bioreactor chamber conforming to a cavity of the mold.
Figure 10:
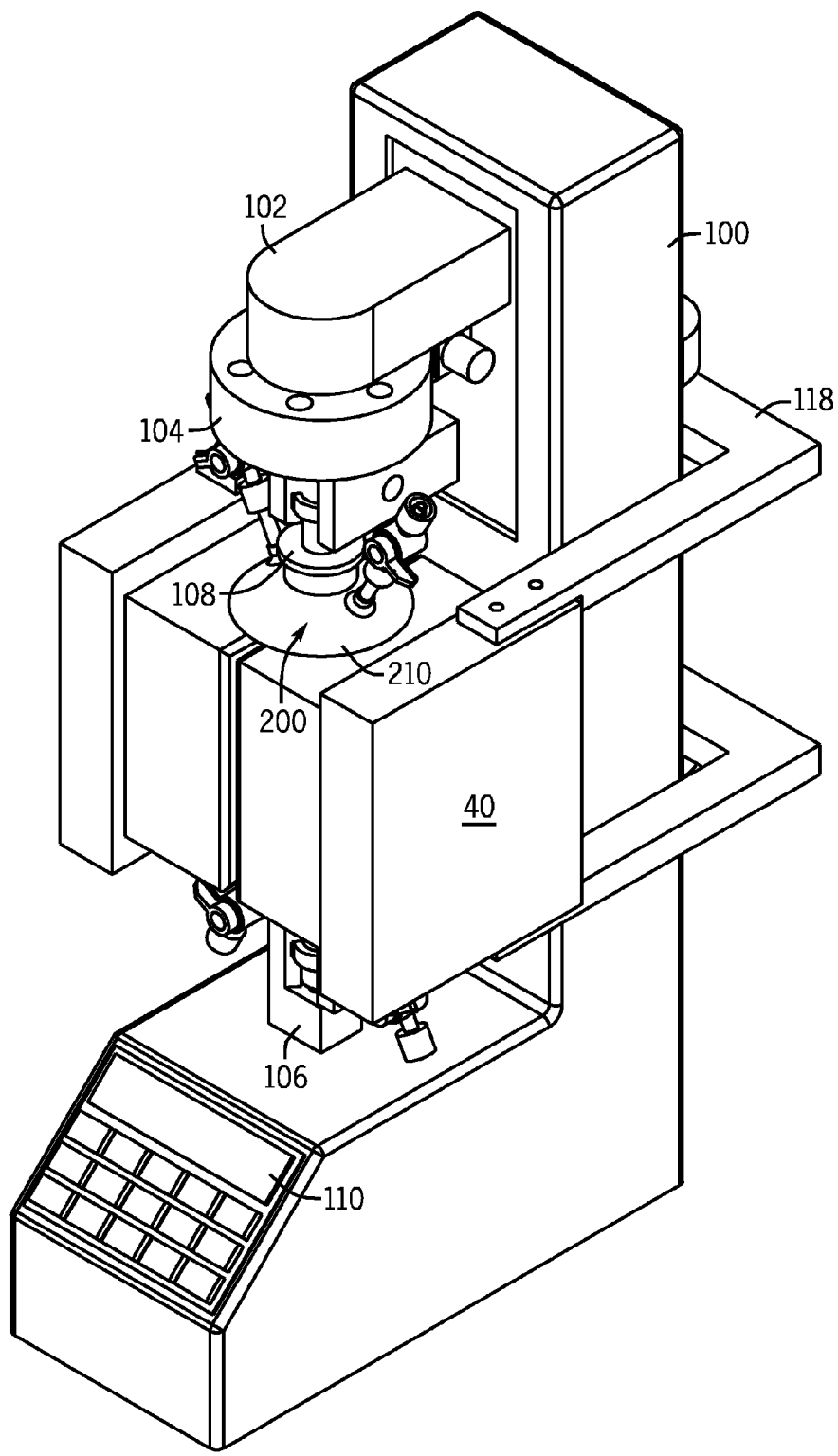
FIG. 10 is a partial section perspective view of a bioreactor and bioreactor chamber in accordance with an embodiment of the invention showing the mold surrounding a portion of the bioreactor chamber.
Figure 11:
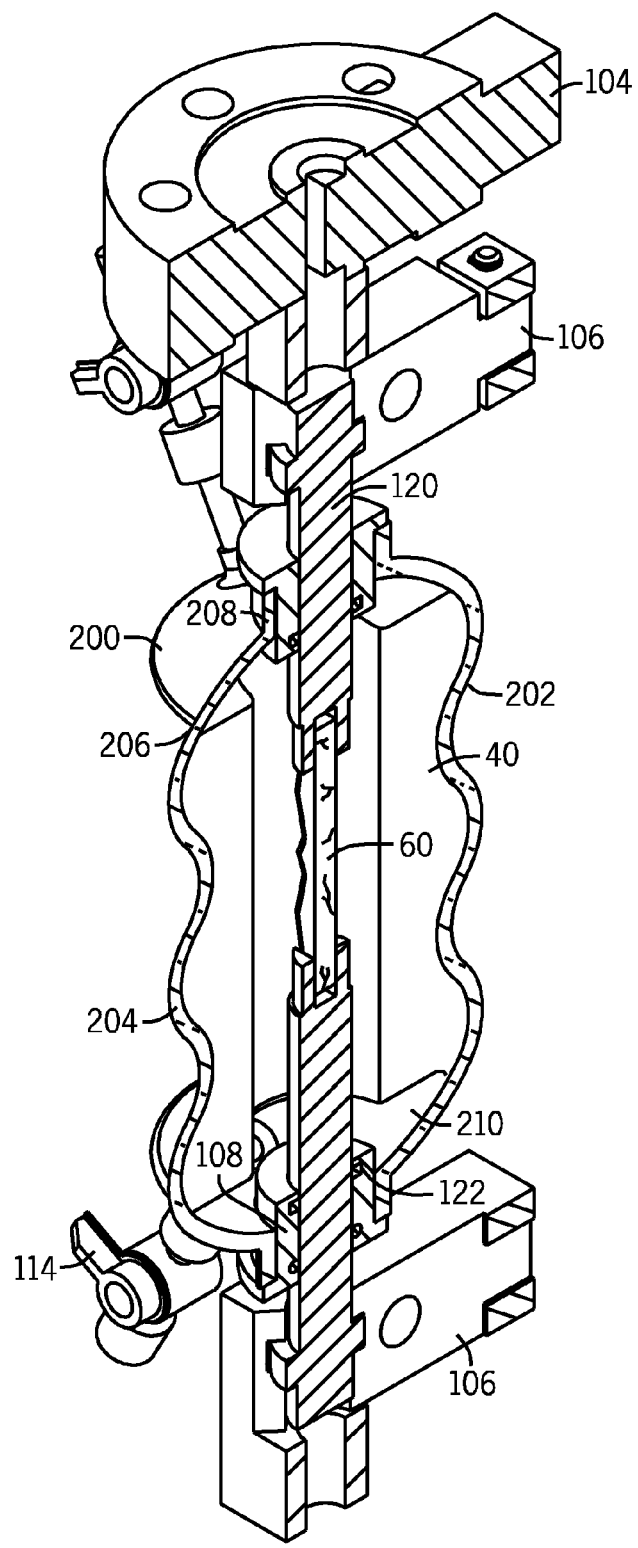
FIG. 11 is a partial sectional perspective view of the bioreactor chamber of the type shown in FIG. 9, shown coupled to a portion of a bioreactor but removed from the mold and showing conformance with the mold cavity shape.

Referring now to FIGS. 9-11, the bioreactor 10 is shown having the mold 40 articulated into position, such that the mold cavity constricts a portion of the chamber 20. A portion 210 of the sheath 200 overlaps upper and lower ends of the mold 40. The sheath 200 conforms to the shape of the cavity as illustrated in FIG. 11. In an embodiment not shown, the mold and mold cavity could be sized to encompass the entire chamber 20 within the mold cavity, whereby the entire sheath 200 would conform to the shape of the cavity. During seeding, a high concentration of cells in a small volume of media is delivered into the chamber through port 112. After a desired lapse of time, the mold 40 is articulated away from the chamber and culture media or nutrients are introduced through the ports 112 to fill the sheath 200 and increase the volume of the chamber 20. The volume of the chamber 20 may be adjusted by using the mold to partially constrict the sheath 200.

Those skilled in the art will further appreciate that an expandable outer sheath or membrane 300 may be used to constrict an inner enclosure or membrane 302. Once the cells have been cultured and the desired stimulus has been delivered to the sample, the user may then remove the chamber from the bioreactor 10. The user may, for example, use the indexing frame 500 to grasp the chamber and remove the connectors 108 from the quick disconnect couplings 106. If a strain was being applied to the sample at the time the chamber is removed, the frame may be adjusted so that the separation distance between the grips 120 remain constant, thereby keeping a strain applied to the sample 60.

When transporting the chamber to and from a sterile environment, use of the dual membrane chamber 30 allows the user to transport the chamber in a non-sterile environment while maintaining the sterility of the inner membrane 302. Once transported, the outer membrane 300 may be cut away without affecting the sterility of the inner membrane 302. Likewise, in this manner, the sample may be seeded, cultured, and transported within the inner membrane 302 while maintaining the sterility of the sample.

These and various other aspects and features of the invention are described with the intent to be illustrative, and not restrictive. This invention has been described herein with detail in order to comply with the patent statutes and to provide those skilled in the art with information needed to apply the novel principles and to construct and use such specialized components as are required. It is to be understood, however, that the invention can be carried out by specifically different constructions, and that various modifications, both as to the construction and operating procedures, can be accomplished without departing from the scope of the invention. Further, in the appended claims, the transitional terms comprising and including are used in the open ended sense in that elements in addition to those enumerated may also be present. Other examples will be apparent to those of skill in the art upon reviewing this document.

The invention claimed is:

1. A method of seeding and culturing a sample within a chamber, comprising the steps of:
    positioning a sample within a chamber capable of retaining a fluid and having a first volume and second reduced volume;
    seeding cells on the sample in the second reduced volume of the chamber;
    after said step of seeding cells, culturing the cells on the sample in the first volume of the chamber;
    engaging the sample between first and second grips in the first volume; and
    at least one of applying a linear force to the sample via the first and second grips and applying a torque to the sample via the first and second grips.

2. The method of claim 1, further comprising varying a volume of the chamber between the first volume and second volume.

3. The method of claim 1, further comprising transporting the chamber while applying a linear force to the sample.

4. The method of claim 1, further comprising transporting the chamber with a strain on the sample.

5. The method of claim 1, further comprising transporting the chamber with a torque applied on the sample.

6. The method of claim 1, further comprising setting a repeatable gauge length of the sample.

7. The method of claim 1, further comprising transporting the sample in a sterile chamber.

8. The method of claim 7, further comprising transporting the sample without removing the sample from the chamber in which cells are seeded and cultured on the sample.

9. The method of claim 1, wherein the chamber includes a first deformable outer membrane and second deformable inner membrane.

10. A method of seeding and culturing a sample within a chamber, comprising the steps of:
    positioning a sample within a chamber capable of retaining a fluid and having a first deformable outer sheath and second deformable inner enclosure;
    seeding cells on the sample in the second deformable inner enclosure;
    after said step of seeding cells, culturing the cells on the sample in the second deformable inner enclosure of the chamber; and
    engaging the sample between first and second grips in the second deformable inner enclosure of the chamber; and
    at least one of applying a linear force to the sample via the first and second grips and applying a torque to the sample via the first and second grips.

11. The method of claim 10, further comprising varying a volume of the chamber between a first volume and a second volume.

12. The method of claim 10, further comprising transporting the chamber while applying at least one of a linear force, a strain, and a torque on the sample.

13. The method of claim 10, further comprising setting a repeatable gauge length of the sample.

14. The method of claim 10, further comprising transporting the sample without removing the sample from the second deformable inner enclosure in which cells are seeded and cultured on the sample.

15. A method of seeding and culturing a sample within a chamber, comprising the steps of:
    positioning a sample within a chamber capable of retaining a fluid and having a first deformable outer sheath and second deformable inner enclosure, and said chamber having a first volume and second reduced volume ;
    seeding cells on the sample in the second deformable inner enclosure;
    after said step of seeding cells, culturing the cells on the sample in the second deformable inner enclosure of the chamber;
    engaging the sample between first and second grips in the second deformable inner enclosure of the chamber; and
    at least one of applying a linear force to the sample via the first and second grips and applying a torque to the sample via the first and second grips.

16. The method of claim 15, further comprising varying a volume of the chamber between a first volume and a second volume.

17. The method of claim 15, further comprising transporting the chamber while applying at least one of a linear force, a strain, and a torque on the sample via the first and second grips.

18. The method of claim 15, further comprising seeding cells on the sample in the second reduced volume of the chamber.

19. The method of claim 15, further comprising culturing the cells on the sample in the first volume of the chamber.

* * * * *